United States Patent
Hu et al.

(10) Patent No.: US 9,810,660 B2
(45) Date of Patent: Nov. 7, 2017

(54) FIN-FET SENSOR WITH IMPROVED SENSITIVITY AND SPECIFICITY

(75) Inventors: Wenchuang Hu, Allen, TX (US); Ruhai Tian, Irving, TX (US); Suresh Regonda, Richardson, TX (US); Krutarth B. Trivedi, Plano, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 1027 days.

(21) Appl. No.: 13/876,958

(22) PCT Filed: Sep. 28, 2011

(86) PCT No.: PCT/US2011/053631
§ 371 (c)(1),
(2), (4) Date: Jun. 16, 2013

(87) PCT Pub. No.: WO2012/050873
PCT Pub. Date: Apr. 19, 2012

(65) Prior Publication Data
US 2013/0291627 A1    Nov. 7, 2013

Related U.S. Application Data

(60) Provisional application No. 61/387,903, filed on Sep. 29, 2010.

(51) Int. Cl.
*H01L 29/76* (2006.01)
*G01N 27/403* (2006.01)
*G01N 15/06* (2006.01)
*G01N 27/414* (2006.01)
*H01L 27/12* (2006.01)
*H01L 29/78* (2006.01)

(52) U.S. Cl.
CPC ..... *G01N 27/4145* (2013.01); *G01N 27/4146* (2013.01); *H01L 27/1211* (2013.01); *H01L 29/785* (2013.01)

(58) Field of Classification Search
CPC ....... H01L 29/76; G01N 27/403; G01N 15/06
USPC ............ 257/213, 253; 422/50, 68.1, 82.01; 436/43, 149, 150, 151
See application file for complete search history.

(56) References Cited

U.S. PATENT DOCUMENTS

| | | | |
|---|---|---|---|
| 2005/0014178 A1* | 1/2005 | Holm-Kennedy | ................ 435/6 |
| 2005/0095389 A1* | 5/2005 | Newns | ..................... G11B 9/02 428/64.4 |
| 2006/0284273 A1* | 12/2006 | Ho | .................... H01L 27/14603 257/428 |
| 2009/0050982 A1 | 2/2009 | Pantisano et al. | |
| 2009/0127592 A1 | 5/2009 | El-Kareh et al. | |
| 2010/0066348 A1 | 3/2010 | Merz et al. | |
| 2010/0090302 A1* | 4/2010 | Nguyen Hoang | ... H03H 3/0072 257/428 |
| 2010/0194409 A1 | 8/2010 | Gao et al. | |
| 2011/0248320 A1* | 10/2011 | Rothberg et al. | ............. 257/253 |

(Continued)

*Primary Examiner* — Brian J Sines
(74) *Attorney, Agent, or Firm* — Yee & Associates, P.C.

(57) ABSTRACT

The claimed invention is directed to a finFET biosensor with improved sensitivity and selectivity. Embodiments of the invention are also directed to finFET biosensor arrays, methods for operating finFET biosensors with improved sensitivity and selectivity, and methods of operating finFET biosensor arrays.

21 Claims, 20 Drawing Sheets

(56) References Cited

U.S. PATENT DOCUMENTS

2012/0021918 A1* 1/2012 Bashir .................... B82Y 15/00
   506/2
2012/0282596 A1* 11/2012 Khater ................... B82Y 10/00
   435/5

* cited by examiner

FIN-FET SENSOR WITH IMPROVED SENSITIVITY AND SPECIFICITY

CROSS-REFERENCE TO RELATED APPLICATIONS

This application claims the benefit of priority under U.S.C. §119(e) of U.S. Provisional Application 61/387,903 filed Aug. 29, 2010.

FIELD OF THE INVENTION

The present invention relates generally to electronic sensors based on ion-sensitive field effect transistors (ISFETs). More particularly to Fin FET transistor with nanoscale width channels as sensing elements.

BACKGROUND OF THE INVENTION

Enzyme-Linked Immunosorbent Assay (ELISA) is a commonly used test used for medical diagnostics and to test for the presence of molecular contaminants such as pesticides and water and food contaminants. The ELISA test is very sensitive (~picogram per ml) but takes hours to run by a highly skilled technician. In addition the ELISA test requires several sequential chemical reactions that are time sensitive and handling sensitive. Expensive optical equipment is required to read the results.

Electronic sensors such as, for example, biochemical and ion sensitive field effect transistors (bio-FETs and ISFETs) overcome the key limitations of optical sensors. They are a low cost, one step test that gives results in a manner of minutes and do not require a highly trained technician to run the test or expensive optical equipment to read the test.

FETs are natural candidates for electrically-based sensing of charged analytes due to the dependence of channel conductance on both gate voltage and surface charges resulting from the binding of biomolecules to the channel surface. ISFETs have been developed for over 30 years and are reliable electronic biochemical sensors for real-time measuring pH values of liquid and in-line quality monitoring of milk, beer, yogurt, and the like.

Recently, fin-FETs with nanowidth channels have been developed which provide detection limit down to parts per billion (ppb) for gas detection and femtomolar (fM) or femtogram/ml for detection in solution which is comparable with most advanced optical sensors. The high sensitivity is attributed to nano width (100 nm or less) of the fin-FET channels which are comparable to the device Debye length and size of biomolecules. In nanowidth fin-FETs, the entire channel may be fully modulated by the charge on biomolecules binding to the gate dielectric significantly increasing sensitivity.

As described above, the nanowidth finfET shows great potential in becoming a truly low cost, ultra-portable, and highly sensitive sensor platform for meeting future biosensing applications. However, there are still important challenges for this type of sensor to be practically useful. The challenges may be, for example, poor stability, poor reproducibility, and poor reliability when using physiological samples such as, for example, whole blood, serum, saliva, and the like. The poor reliability of device itself and their bio-abio surfaces means that at present finFET biosensors cannot be made reproducibly and uniformly.

SUMMARY OF THE INVENTION

The following presents a simplified summary in order to provide a basic understanding of one or more aspects of the invention. This summary is not an extensive overview of the invention, and is neither intended to identify key or critical elements of the invention, nor to delineate the scope thereof. Rather, the primary purpose of the summary is to present some concepts of the invention in a simplified form as a prelude to a more detailed description that is presented later.

An embodiment of the invention is directed to a finFET biosensor, comprising: a semiconductor layer on a silicon-on-insulator (SOI) substrate; a transistor source; a transistor drain; one or more finFET nanochannels formed in said semiconductor layer, wherein said nanochannels connect said transistor source and said transistor drain; a gate dielectric covering a portion of said one or more nanochannels; a sample channel; and a sensor region further comprising a sensor molecule, wherein said sensor molecule is coupled to said gate dielectric, and further wherein the sensor region is located within the sample channel.

Another embodiment of the invention is directed to a method of operating a finFET biosensor comprising the steps: flowing a sample with a target molecule through a sample channel of said finFET biosensor; measuring a sample electrical signal of said finFET biosensor transistor; and correlating said sample electrical signal to a sample concentration of said target molecule.

A further embodiment of the invention is directed to a finFET array comprising: a plurality of finFET biosensor transistors devices having a plurality of sensor regions where said plurality of sensor regions are located within the same sample channel.

Other embodiments of the invention are directed to methods of operating a finFET biosensor and methods of operating a finFET biosensor array.

DETAILED DESCRIPTION OF EXEMPLARY EMBODIMENTS

Figure 1A:
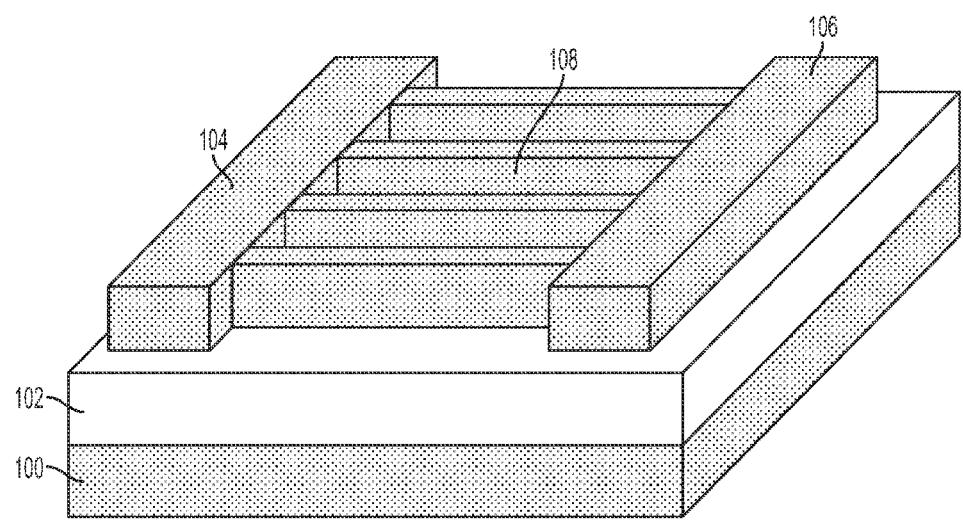
FIGS. 1A and 1B represent views of a finFET biosensor.

The claimed invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The term "sensor molecule" refers to a molecule that selectively binds with a molecule whose concentration is to be measured in a sample. For example, a sensor molecule may be an antibody, an antigen, a protein, a receptor, an aptamer, a peptide, a DNA strand, or an enzyme. The sensor molecule is attached to the gate dielectric of a finFET. When the sensor molecule binds with its target molecule the charge surrounding the channel of the finFET transistor may be changed. This change in charge causes the conductance of the finFET transistor channel to change. When the finFET biosensor transistor is biased in the subthreshold region, a linear change in the charge from target molecules that are attached to the sensor molecules surrounding the finFET nanochannel causes a logarithmic change in the conductance of the finFET nanochannel.

The term "target molecule" refers to the molecule whose concentration is to be measured in a sample. The sensor molecule selectively binds with the target molecule. In many instances a sensor molecule such as an antibody may be formed that is specific to a target molecule such as a protein. Sometimes, however, as in the case of the thyroid hormone T4 the molecule is small and uncharged and antibodies cannot be formed by injecting T4 molecules directly into an animal. For these cases the T4 is attached to a hapten molecule such as bovine serum albumin (BSA) forming a target-hapten molecule that is injected into a host animal. The immune response to the T4-BSA (target-hapten) molecule is strong and the antibody thus formed is selective to both the T4-BSA molecule and also to individual T4 molecules.

For example, if the sensor molecule is the antibody to thyroid hormone, T4, it will selectively bind to the T4 hormone even though the sample may contain many other similar hormone molecules such as the thyroid hormone, T3 (T3 and T4 molecules are formed of 33 atoms having identical structures. The only difference is that one hydrogen atom in T3 is replaced with an iodine atom to form T4.) When the sensor molecule is an antibody, the target molecule is referred to as an antigen.

The term "semi orthogonal sensor molecules" refers to two or more sensor molecules where one of the sensor molecules is specific to a target molecule and other sensor molecules are cross-reactive or exhibit non-selectively to the target molecule. The other sensor molecules may bind to several molecules in addition to the target molecule.

In an embodiment of the claimed invention, the target molecule may be an antigen such as insulin for example. In these applications the antibody to insulin is attached to the gate dielectric of the finFET biosensor. When the finFET biosensor is immersed in a sample containing insulin, the insulin antibody that is attached to the gate will bind to insulin antigen in the sample changing the conductance of the finFET biosensor transistor depending upon the concentration of the insulin antigen in the sample.

In other embodiments of the claimed invention, the target molecule may be an antibody such as in the diagnosis of pulmonary tuberculosis. In these applications, the concentration of the antibody in the sample needs to be measured. In these applications the antigen can be bound to the gate dielectric of the finFET biosensor transistor and used as the sensor molecule to detect concentration of antibody in the sample. For example, the pulmonary tuberculosis antigen may be attached to the gate dielectric of the finFET biosensor. When the finFET biosensor is immersed in a sample containing pulmonary tuberculosis antibodies, the antibodies in the sample bind to the pulmonary tuberculosis antibodies on the gate dielectric changing the conductance of the finFET biosensor transistor depending upon the concentration of the pulmonary tuberculosis antibodies in the sample.

The term "signals" of a finFET biosensor refers to both the directly measured electrical parameters and/or derived parameters from the measured electrical parameters of the sensor device. The detected signals of the sensor can be in many forms. For directly measured signals, there can be several different biasing and configurations. One way is to bias the source and drain with a known voltage and also bias a gate electrode with another known voltage, measure the drain current during sensing experiments. Another way is to bias the source and drain with a current source and bias a gate electrode with a known voltage, measure the drain voltage during sensing. A third way is to bias the source and drain with a known voltage, sweep the voltage of gate electrode in a chosen voltage range, and simultaneously measure the drain current, and then to generate a standard I-V curve of the transistor.

The signals can also be indirect measurements or derived parameters from direct measurement results as outlined above. Here to give several examples. First, with measured electrical parameters, one can derive the change of these parameters by subtracting the measured values from the initial value measured before the sensing or measured using a standard sample. A percentage of change can further be derived by dividing the relative change by the initial value. In addition, the transistor conductance can be derived by dividing the measured drain current by the drain voltage, or the trans-conductance of the transistor can be derived by dividing the measured drain current by the voltage of gate electrode. With the measured I-V curve of the transistor, threshold voltage and change or shift of threshold voltages, etc may be extracted. All of these direct or indirect transistor signals can be used to analyze detection results and be correlated to the concentration of target molecules. For simplicity, we use conductance of the transistor as an exemplary signal of the sensor device in the following embodiments.

The term "finFET biosensor array" refers to a finFET biosensor device with more than one finFET biosensor transistor where the sensor area of each finFET biosensor transistor is exposed to the same sample. When a sample is input to the finFET biosensor array it immerses the sensor area of all the finFET biosensor transistors in the finFET biosensor array. The individual finFET biosensor transistors may have different fin widths to detect different target molecule concentration ranges, may have different sensor molecules attached to detect different target molecules in the sample, or may have semi-orthogonal antibodies attached to the different finFET biosensor transistors.

Figure 10A:
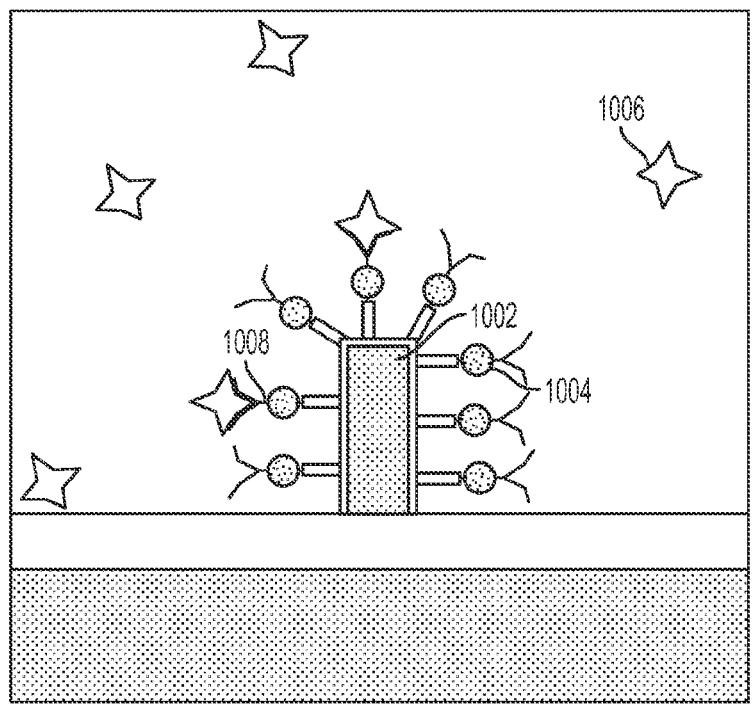
FIG. 10 is an illustration of detecting target molecules using finFETs.
Figure 10B:
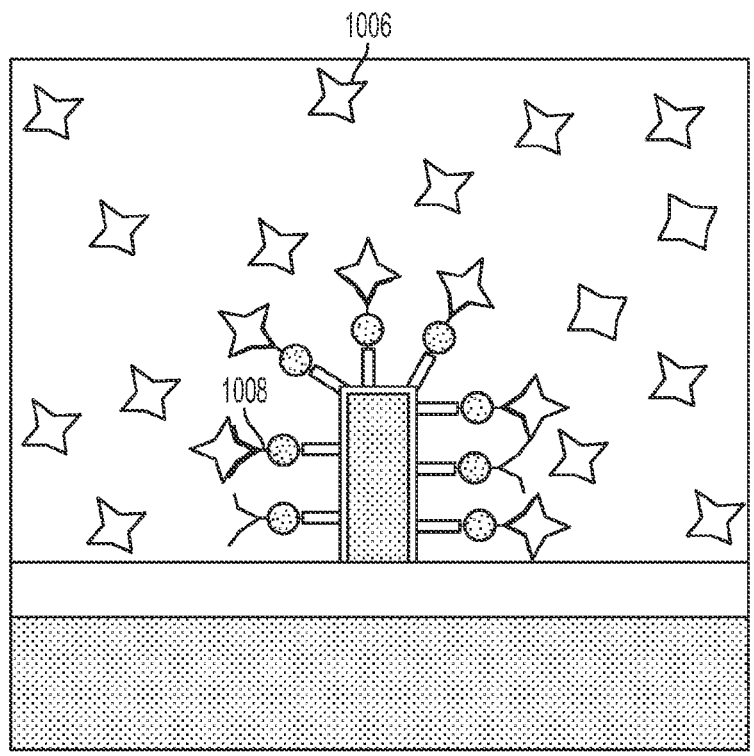

For most target molecules the concentration in a sample may be directly measured as is illustrated in FIGS. 10A and 10B. As shown in FIG. 10A, if the concentration of target molecule 1006 is low, few of the target molecules 1006 will bind to the sensor molecules 1004 that are immobilized on the fin 1002. Since few target molecule—sensor molecule complexes form, the fin channel conductance changes little.

If, however, the sample contains a high concentration of target molecules 1006 as shown in FIG. 10B, many target-molecule—sensor molecule complexes 1008 form causing a large change in fin channel conductance. In a direct measure assay the change is fin conductance as measured by the finFET biosensor transistor current is directly proportional to the concentration of target molecule in the sample.

In some instances, target molecules may be small or have insufficient charge to change the conductance of the finFET biosensor channel by the amount required to detect the concentration of the target molecule in a sample with the required sensitivity. For these cases, the target molecule may be bound to the fin as shown in FIGS. 11A and 11B and competitive binding of the sensor molecule may be used.

Figure 11A:
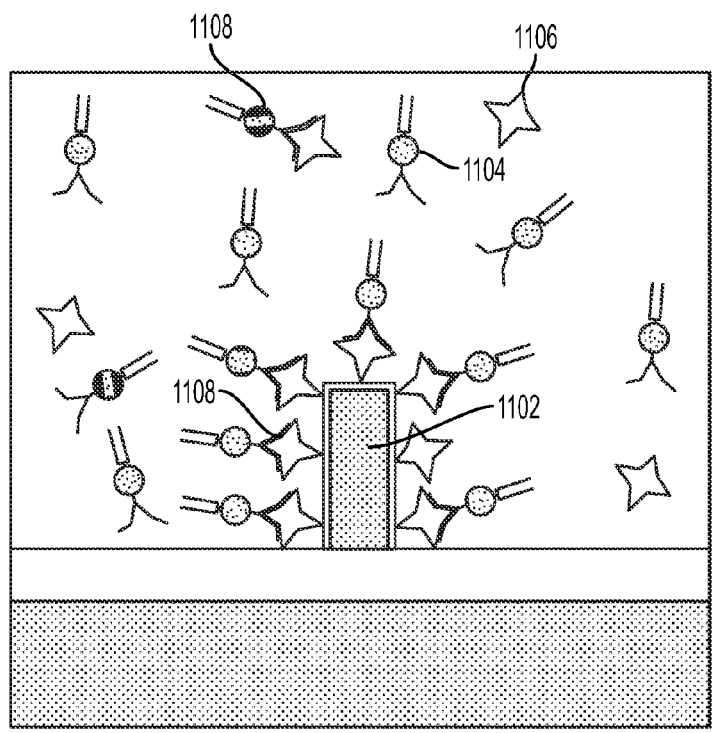
FIG. 11 is a method of detecting target molecules using competitive binding assay with finFETs.

As shown in FIG. 11A, the target molecule 1106 may be bound to the fin 1102 of the finFET biosensor. A known amount of sensor molecule 1104 is then added to the sample solution before the fin is immersed in the sample. If the sample contains little of the target molecule 1106 as shown in FIG. 11A, many sensor-target molecule complexes 1108 will form on the surface of the fin 1102. Since sensor molecules typically carry significant charge, the conductivity of the fin channel is significantly changed.

Figure 11B:
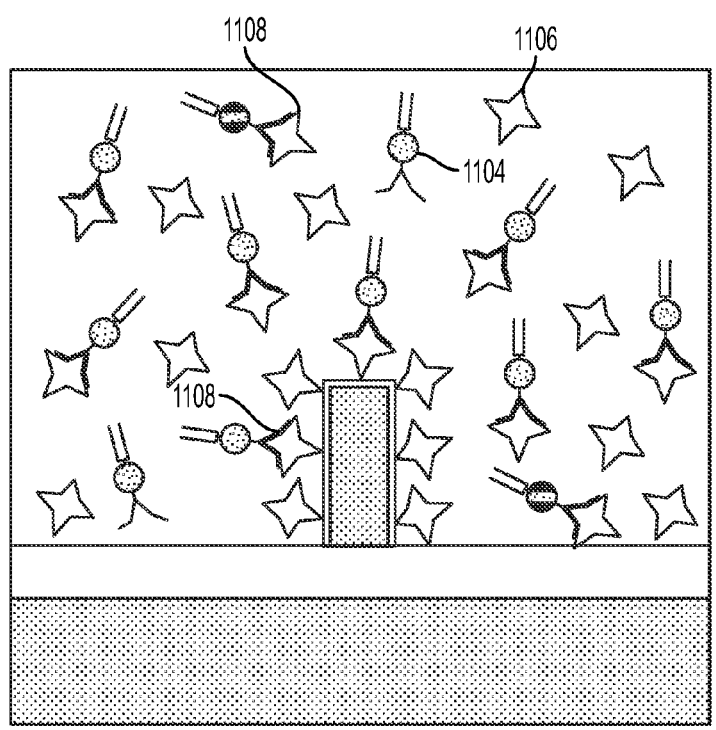

If, however, as shown in FIG. 11B, the sample solution contains a significant concentration of target molecules 1106, much of the known amount of sensor molecule 1104 that is added to the sample will form sensor-target molecule complexes 1108 in the solution leaving few free sensor molecules 1104 to form sensor-target molecule complexes 1108 bound to the fin 1102 and change the fin conductivity. The change in conductivity of the fin is inversely proportional to the concentration of the target molecule in the sample in a sensor molecule competitive binding assay.

Figure 12A:
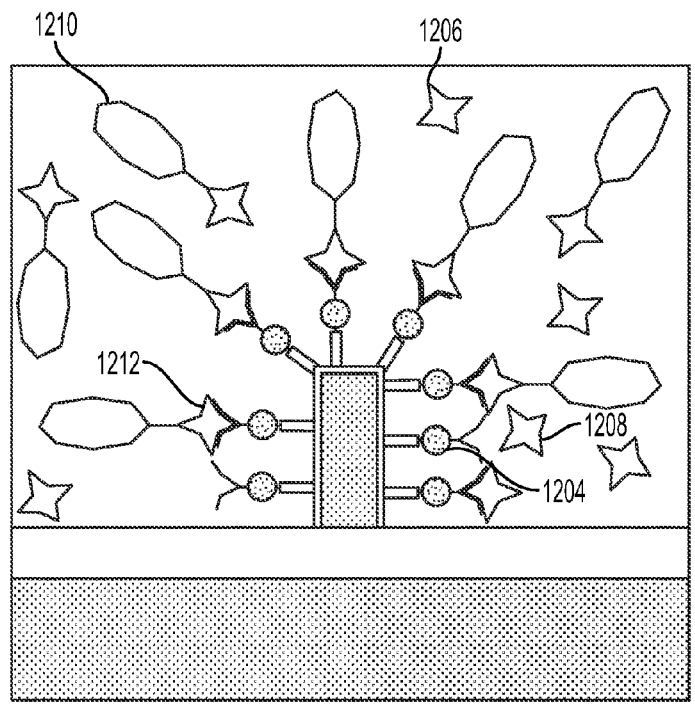
FIG. 12 is a method of detecting target molecules using target-hapten molecules in a competitive binding assay with finFETs.
Figure 12B:
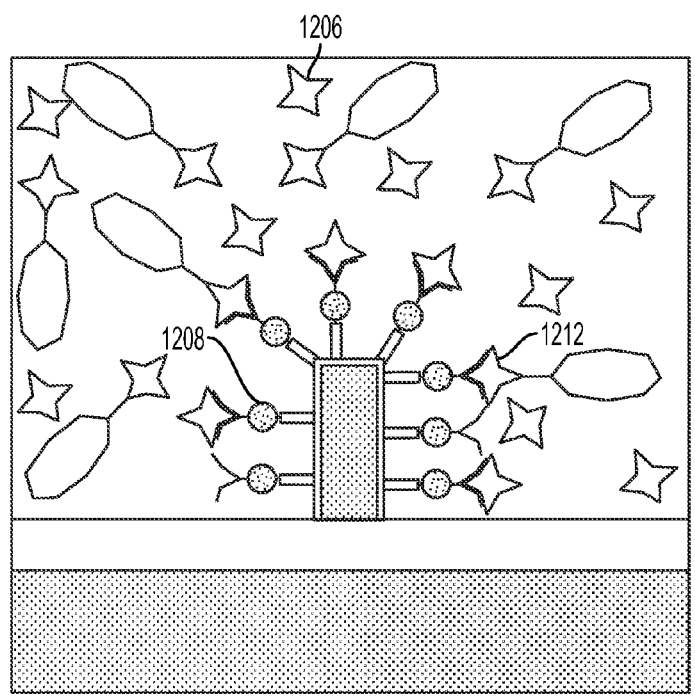

Alternatively, as shown in FIGS. 12A and 12B, if the target molecule 1206 is too small or lacks sufficient charge to change the conductance of the finFET biosensor when it binds to the sensor molecule 1204, a known concentration of target-hapten molecule 1210 may be added to the sample. As shown in FIG. 12A if the sample has a low target molecule concentration 1206, many of the target-hapten molecules 1210 will bind to the sensor molecules 1204 on the fin, forming sensor-molecule-target-hapten molecule complexes 1212. Since haptens typically carry significant charge, the conductance of the fin channel may be change significantly.

Alternatively as shown in FIG. 12B, if the sample contains a high target molecule concentration 1206, few target-hapten molecules 1210 may bind to the sensor molecules 1204 immobilized on the fin causing little change in fin conductance. In this type of target-hapten molecule competitive binding assay the concentration of target molecule in the sample is inversely proportional to the change in fin conductance.

Figure 13:
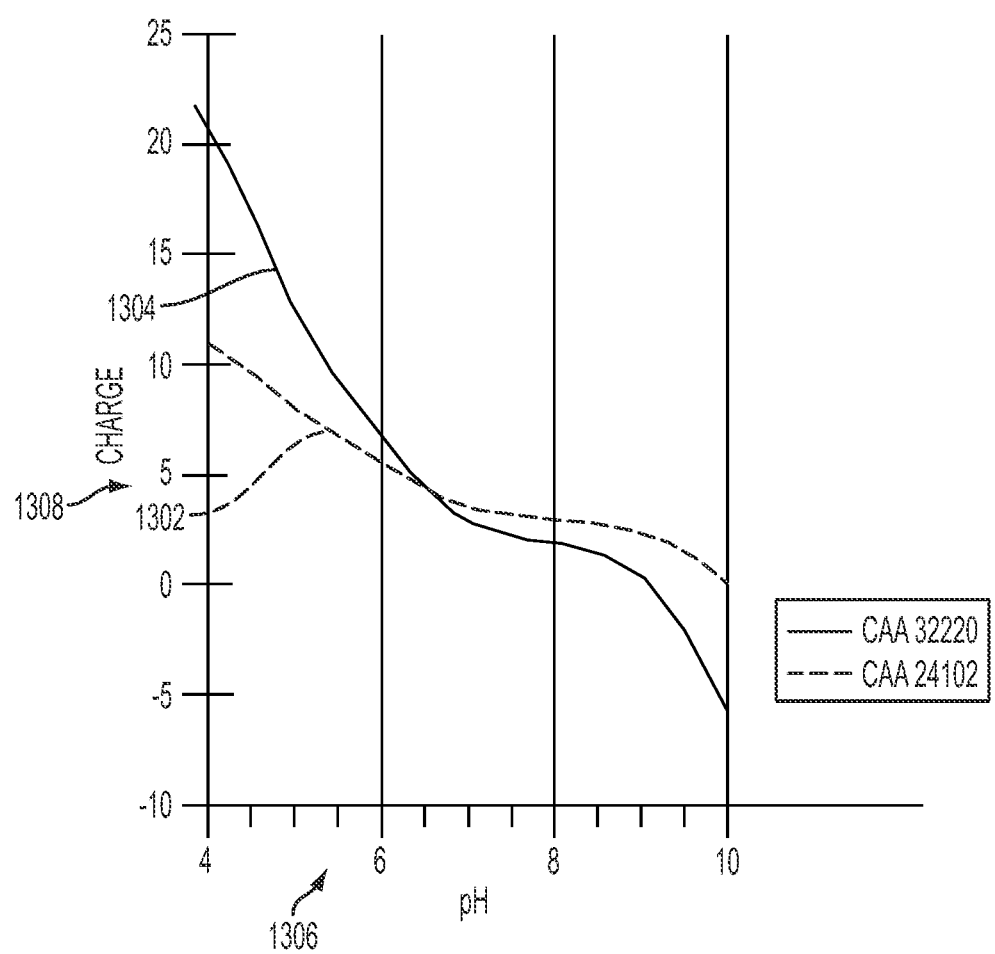
FIG. 13 is a two-dimensional method of detecting target molecules using the charge-pH correlation or dependence of the target molecules.

Two-dimensional detection of target molecule can be achieved using pH values as another parameter in addition to the sensor signals measured. As shown in FIG. 13, sweeping the pH values 1306 of the sample solution containing target molecule, e.g. CAA 24102, during the sensing experiments, a graph 1302 of charge 1308 of target molecule vs. solution pH values 1306 can be generated. The charge 1308 of target molecule can be derived from measured finFET conductance or voltage shift, before plotting the graph 1302. For a different target molecule, e.g. CAA 32220, in the sample solution, a similar experiments of pH sweeping can be performed and generate another graph 1304 for the second target molecule CAA 32220. Two types of target molecules can be clearly differentiated using the shape information, such as slopes, peaks, and valleys, of the graph 1302 vs. 1304, providing a finger-print signature to significantly improve detection specificity.

Figure 14:
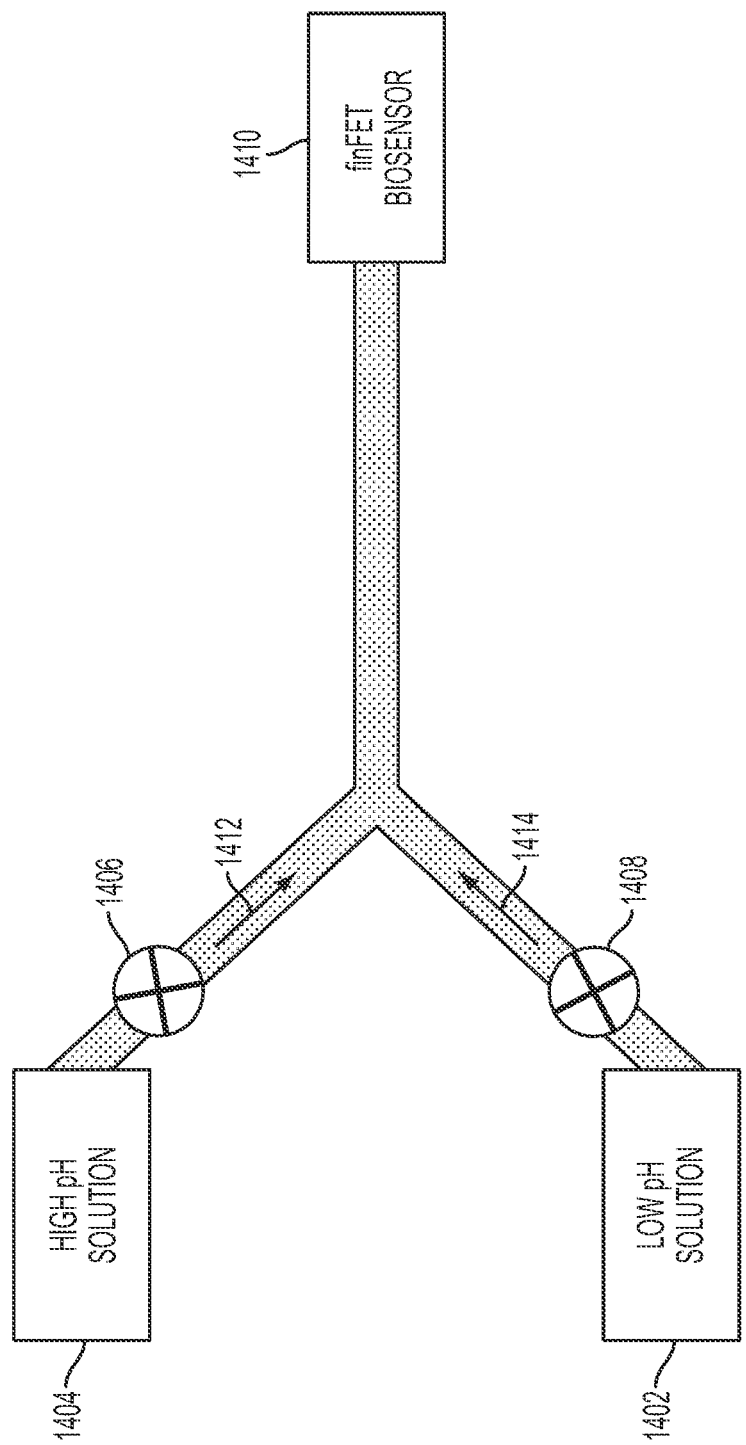
FIG. 14 is an apparatus to measure the charge-pH correlation of the target molecules.

In an embodiment of the invention, a setup to achieve two-dimensional test is shown in FIG. 14. A sample solution containing target molecule 1402 is prepared to have a low pH value and is connected to a fluidic pump or valve 1408. The same sample solution is prepared to have a high pH value 1404 and is connected to another fluidic pump or valve 1406. These two fluidic inlets 1406 and 1408 are merged to the same channel of finFET sensor 1410. Solution flow rates of high pH 1412 and low pH 1414 into the sensor 1410 are controlled coordinately. For instance, if the high pH flow rate 1412 is swept from zero to maximum linearly, then the low pH flow rate 1414 is swept from maximum to zero simultaneously with the same linearity, resulting in a continuously and linearly swept pH values from low 1402 to high 1404 in sample solution while maintaining the same concentration of target molecule. The conductance of finFETs is measured continuously during the pH sweep, so that a graph of conductance vs. pH values can be generated, and a graph of charge vs. pH values can be derived as shown in FIG. 13.

Figure 15A:
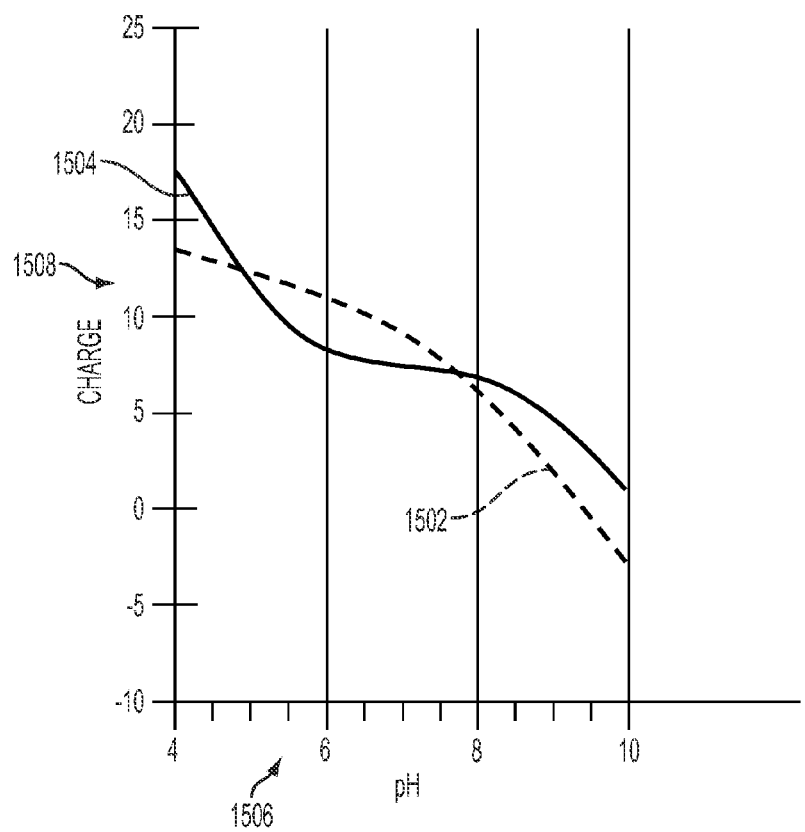
FIG. 15 is a method of a detecting target molecule using its charge-pH correlation and with two semi-orthogonal antibodies.
Figure 15B:
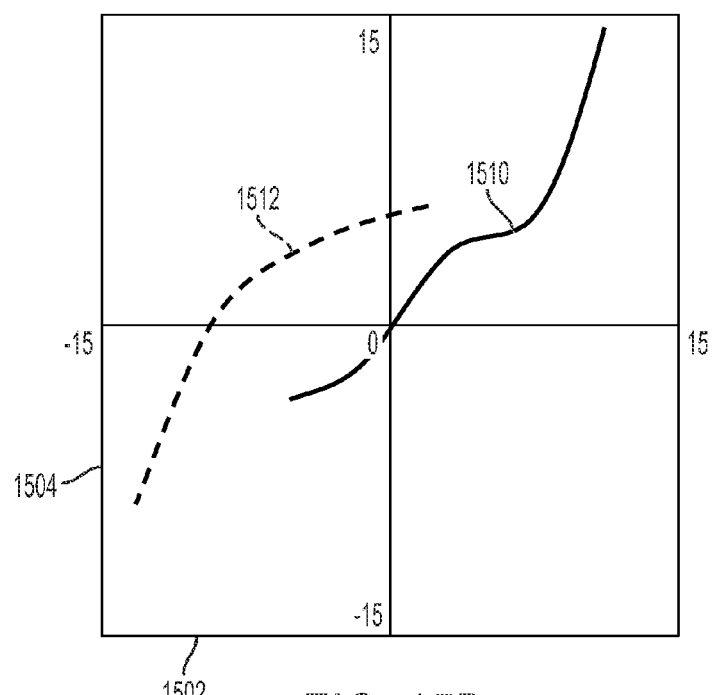
Figure 18:
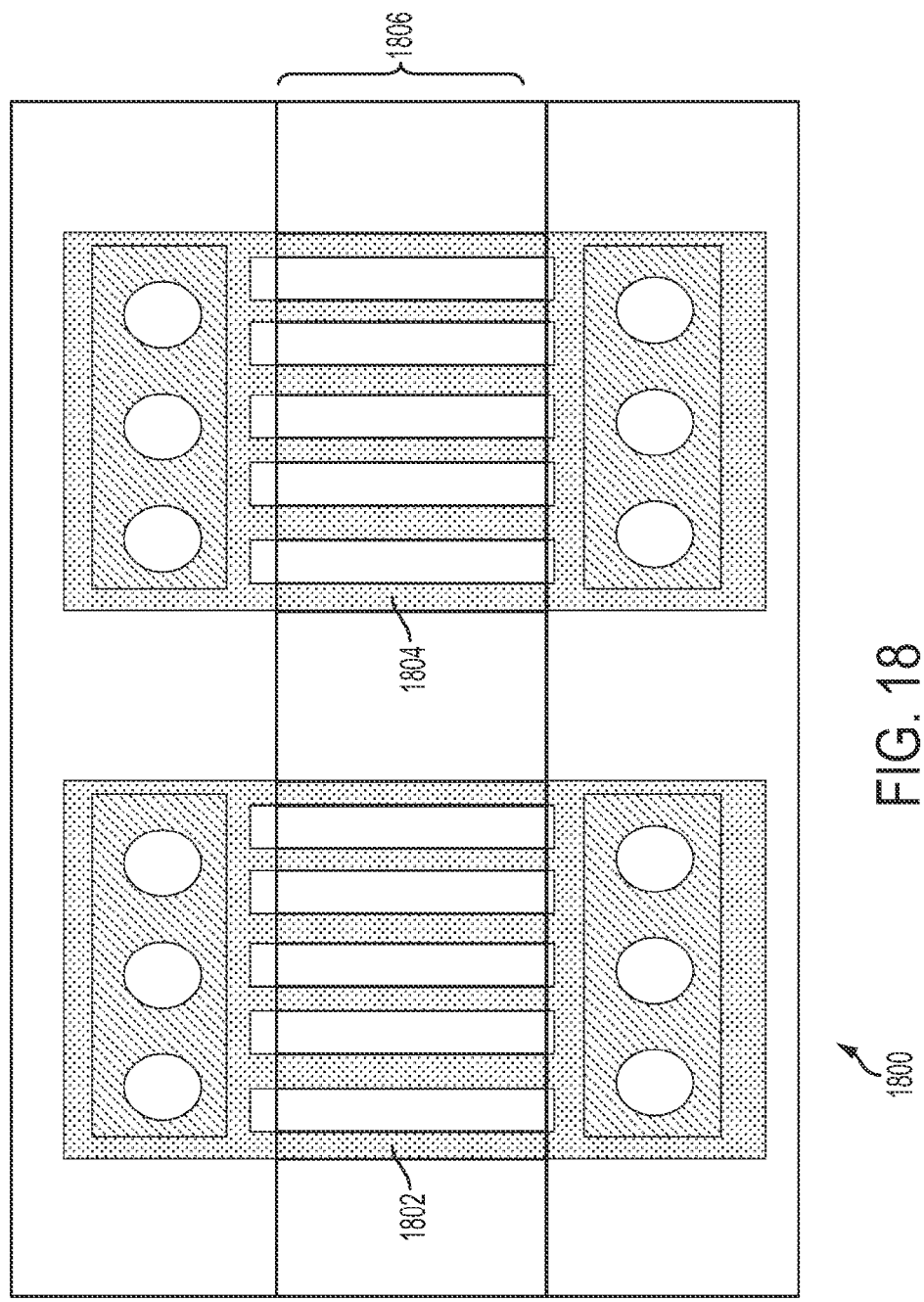

The specificity of detecting the charge of target molecules as a function of solution pH can be further enhanced by using multiple types of semi-orthogonal sensor molecules for the same target molecule, as shown in graphs FIGS. 15A and 15B and in the finFET biosensor array shown in FIG. 18. For example, one antibody that is highly specific to the target molecule can be attached to a first finFET biosensor 1802 in a finFET biosensor array 1800 and used to obtain a first charge-pH graph 1504 following the procedure of FIG. 13. Another antibody that is cross-reactive or non-specific to the same target molecule can be attached to a second finFET biosensor 1804 that is in the same sample channel 1806 and used to obtain another charge-pH graph 1502. Since the charge of target-molecule-sensor-molecule complex depends on the binding specificity and cross-reactivity of antigen-antibody interaction, the two graphs 1502 and 1504 have different shapes. Then for the same pH values, the charge values of two semi-orthogonal sensor molecule-target-molecule complexes can be plotted as shown in FIG. 15B, i.e. specific binding values 1504 as X-axis vs cross-reactive binding values 1502 as Y-axis. The formed curve of the target molecule 1510 in the semi-orthogonal map can be used as a highly specific and accurate fingerprint for the target molecule, since it contains both specific and non-specific binding information of the target molecule. Another type of target molecule 1512 or any non-specific binding of other molecules to the sensor may cause some conductance changes, but will have different locations and shapes in the semi-orthogonal map. This way can enable accurate detection of target molecules with much reduced false positives.

FIG. 1A shows a finFET biosensor transistor with multiple finFET nanochannels, 108, in parallel. The fin-FET sensor transistor is built on a semiconductor on insulator (SOI) substrate composed of substrate 100 and a buried oxide (BOX) layer 102 with a layer of single crystal semiconductor on top in which the finFET biosensor transistor is formed. The finFET biosensor transistor is composed of a source 104 and drain 106, with multiple finFET nanochannels 108 connecting the source 104 and drain 106. The width 120 of the nanochannels 108 is preferably less than about the Debye length of the semiconductor for maximum sensitivity. The Debye length is approximately equal to the distance required for a stationary charge to be shielded by mobile carriers. Maximum change in the finFET nanochannel conductance is achieved when the conductance is modulated throughout the entire width and length of the finFET nanochannel by the target molecule charges.

Figure 1B:
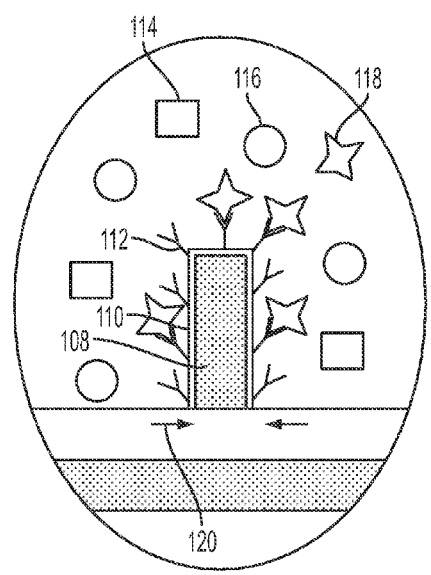

As shown in the cross section through a fin-FET nanochannel in FIG. 1B a gate dielectric 110 is formed over the fin-FET nanochannel 108 and sensor molecules 112 are attached to the gate dielectric 110. The sample solution surrounding the fin-FET nanochannel 108 may contain many different molecules 114 and 116 including the target molecule 118. In the following embodiment, antibodies and antigens are used to illustrate the embodiment. The antibodies, 112, are specific to only the target molecules 118 and will bind only to that antigen 118. Antigens 118 are typically charged so when they bind to the antibody 112 they change the charge on the gate of the finFET nanochannel 108 and therefore change the conductance in the fin-FET nanochannel 108. This changes the current flowing from source to drain in the fin-FET biosensor transistor. A sample with a higher concentration of antigen will bind more antigen and therefore cause a greater change in the conductance of the sensor fin-FET transistor. The change in current through the finFET biosensor can therefore be correlated to the change in concentration of antigen in a sample. The sensitivity of the finFET biosensor transistor depends upon the surface to volume ratio of the finFET nanochannels and also signal to noise ratio of the transistor. Therefore, the sensitivity may be increased by decrease the width and height of Fins; sensitivity can also be enhanced by increasing the number of finFET nanochannels or decreasing the length of the nanochannels due to increased signals to noise ratio. Moreover, increase the number of finFETs can also increase the device uniformity and stability due to reduction of discrete doping effects in the Fins.

Figure 2A:
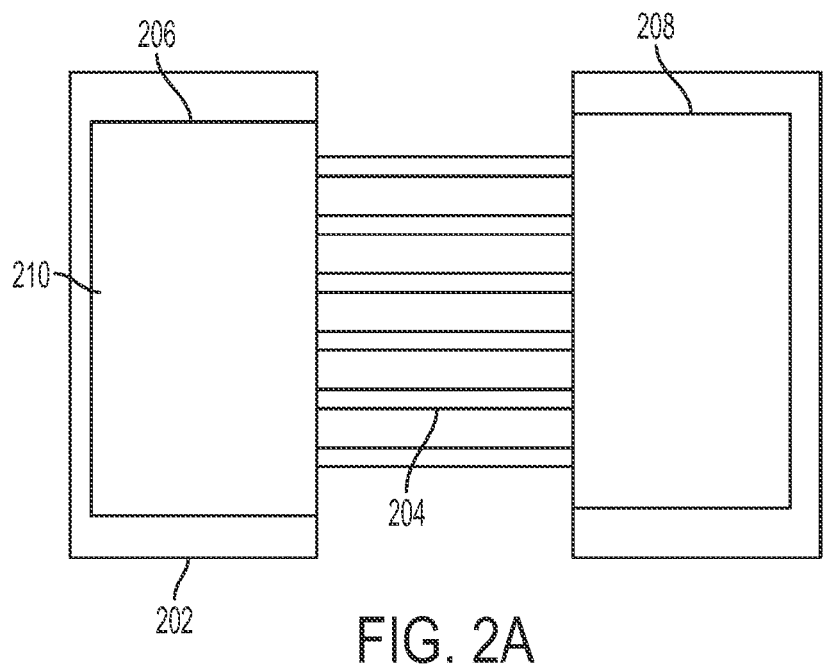
FIG. 2A is a finFET enhancement mode biosensor in accordance with an embodiment of the invention.

In an embodiment of the invention, finFET transistor biosensor may be an enhancement mode MOSFET, a depletion mode MOSFET or a Schottky barrier MOSFET. An embodiment nmos enhancement mode finFET transistor is shown in FIG. 2A. The substrate 202 and the finFET nanochannels 204 in the example embodiment are lightly doped p-type single crystal silicon. The source 206 and drain 208 diffusions are heavily doped n-type 210.

Figure 2B:
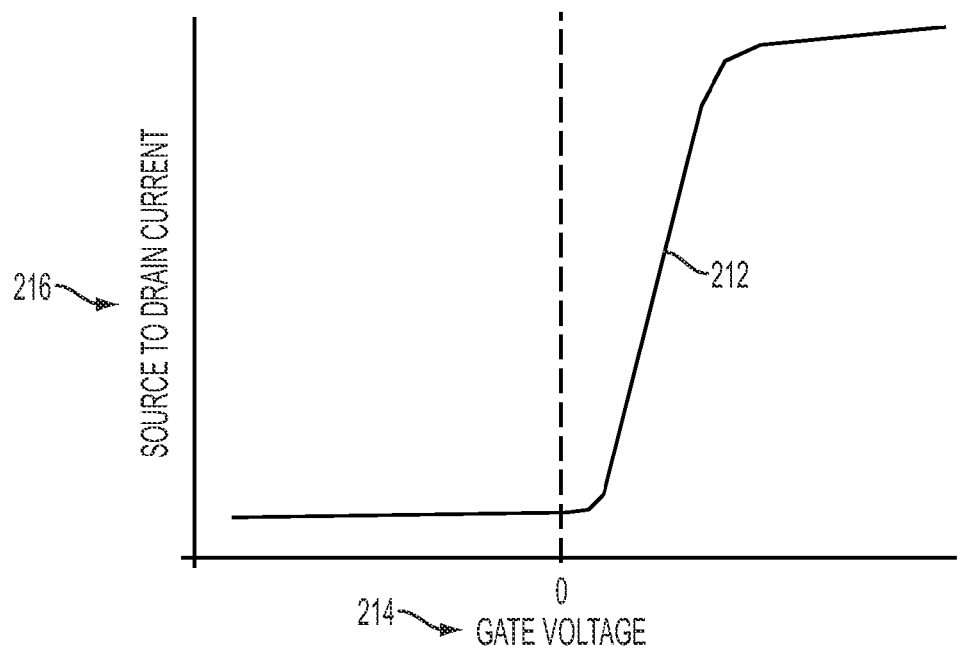
FIG. 2B is an IV curve of an enhancement mode finFET biosensor.

The current 216 versus gate voltage 214 curve for an enhancement mode nmos finFET transistor is shown in FIG. 2B. When the nmos transistor is biased in the subthreshold slope region 212, a small change in the gate voltage 214 causes a large change in the source to drain current 216. Although an nmos finFET enhancement mode transistor is used for illustration, a pmos finFET enhancement mode transistor may also be used.

Figure 3A:
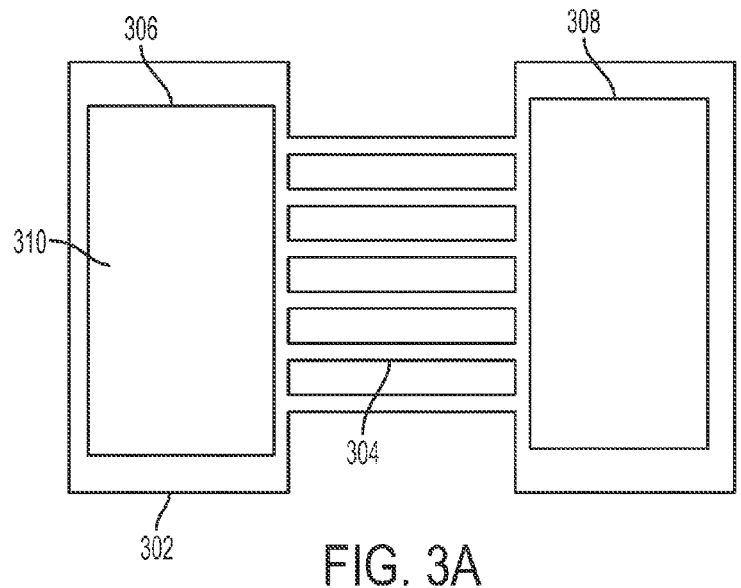
FIG. 3A is a finFET depletion mode biosensor in accordance with an embodiment of the invention.

An embodiment pmos finFET depletion mode transistor is shown in FIG. 3A. The substrate 302 and the finFET nanochannels 304 are lightly doped p-type single crystal silicon. The source 306 and drain 308 diffusions are heavily doped p-type 310.

Figure 3B:
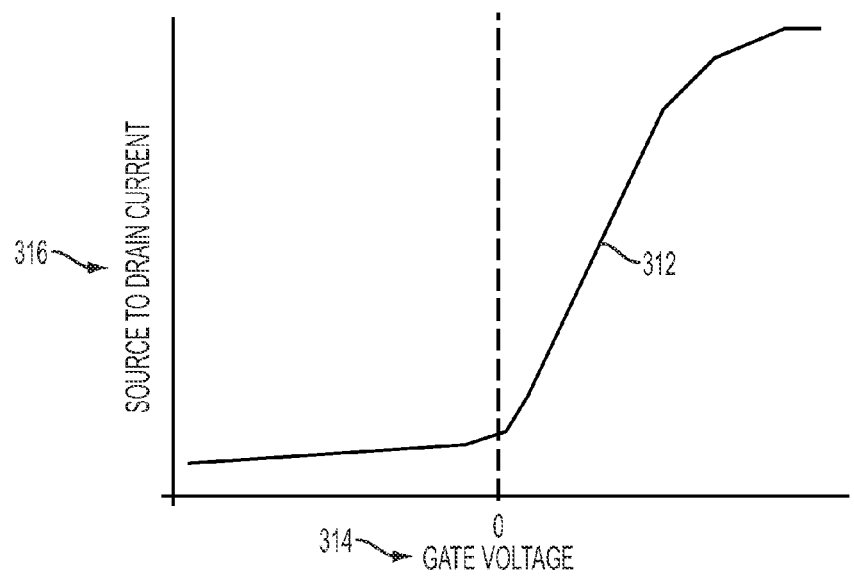
FIG. 3B is an IV curve of a depletion mode finFET biosensor.

The current 316 versus gate voltage 314 curve for a pmos finFET depletion mode transistor is shown in FIG. 3B. When the pmos transistor is biased in the subthreshold slope region 312, a small change in the gate voltage 314 causes a large change in the source to drain current 316. Although a pmos finFET depletion mode transistor is used for illustration, an nmos finFET depletion mode transistor may also be used.

Figure 4A:
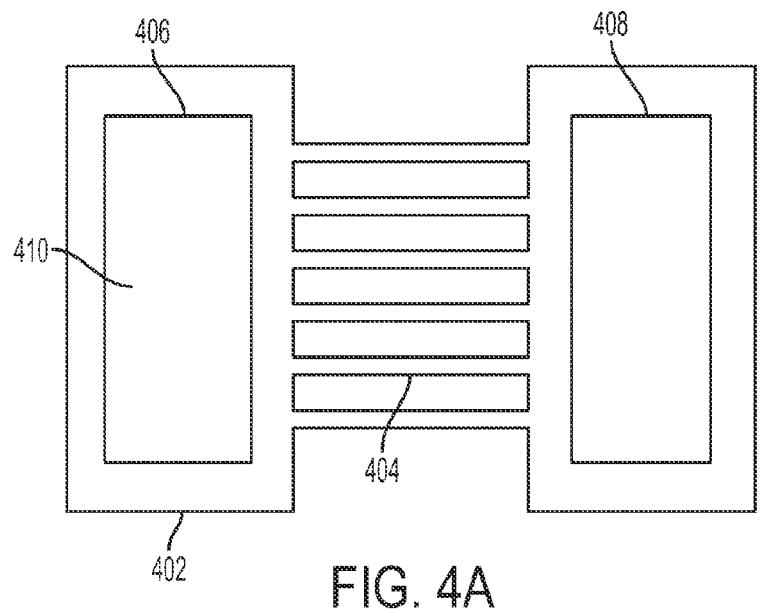
FIG. 4A is a finFET enhancement mode Schottky barrier biosensor in accordance with an embodiment of the invention.

An embodiment pmos enhancement mode Schottky barrier finFET transistor is shown in FIG. 4A. The substrate 402 and the finFET nanochannels 404 are lightly doped p-type single crystal silicon. The source 406 and drain 408 diffusions are also lightly doped p-type single crystal silicon to which Schottky barrier contacts are formed. The Schottky barrier contacts may be formed by depositing a metal such as nickel, titanium, or platinum and then annealing the contact at a temperature in the range of 300° C. to 600° C. in an inert atmosphere such as forming gas, hydrogen, nitrogen, Ar or their mixture.

Figure 4B:
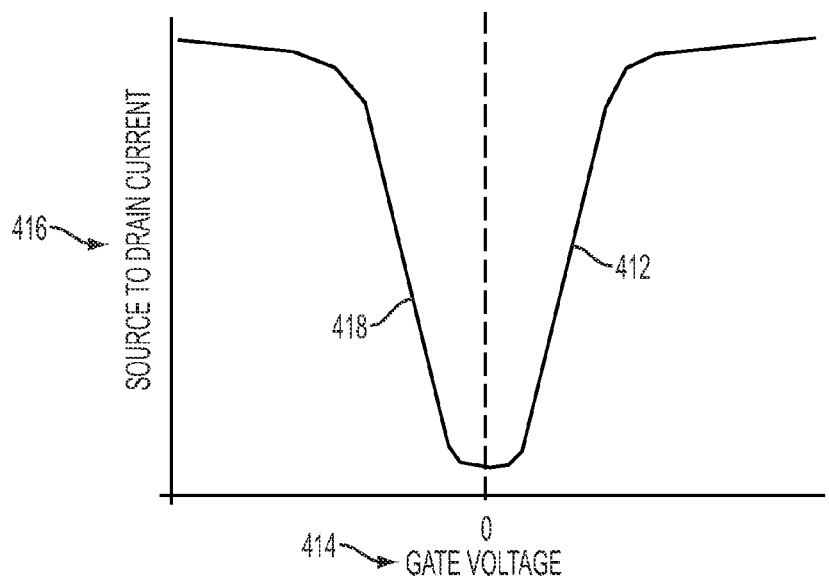
FIG. 4B is an IV curve of an enhancement mode Schottky barrier finFET biosensor.

The current 416 versus gate voltage 414 curve for an enhancement mode pmos finFET transistor is shown in FIG. 4B. As shown in FIG. 4B, the Schottky barrier enhancement mode transistor has a subthreshold slope in both the negative gate voltage 418 and the positive gate voltage 412 regions. This provides the additional advantage of being able to operate the Schottky barrier finFET in both subthreshold slope regions and to compare results. In addition, for a given sensor molecule, detection of the target molecule may have increased sensitivity in one of the two subthreshold slope regions 418 or 412. Although a pmos enhancement mode Schottky transistor is used to illustrate the embodiment, a nmos enhancement mode Schottky transistor may also be used.

Figure 5A:
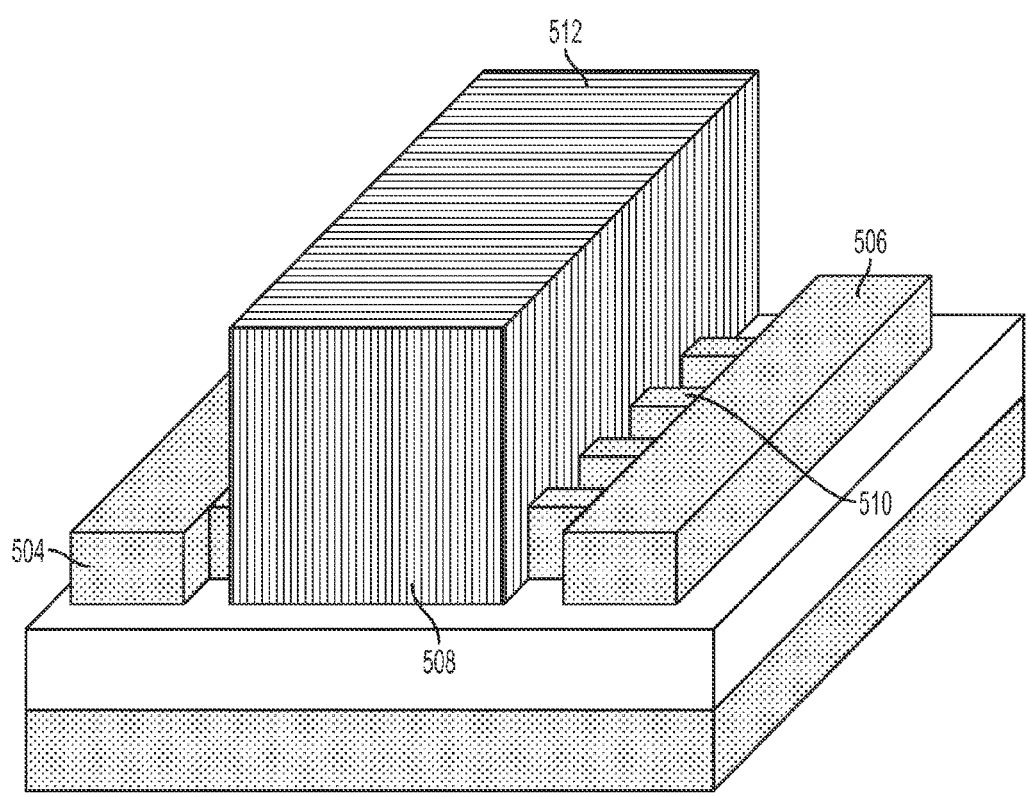
FIGS. 5A through 5C are steps in forming a finFET biosensor according to embodiments of the invention.
Figure 5B:
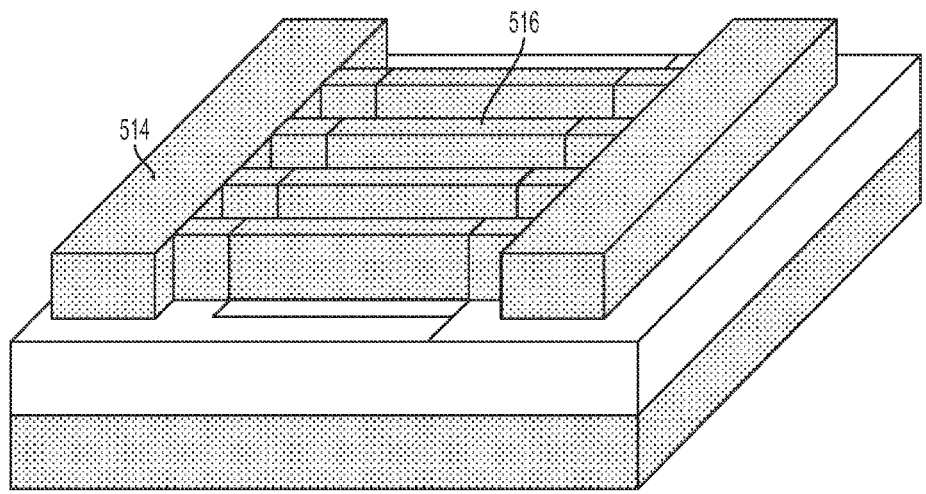
Figure 5C:
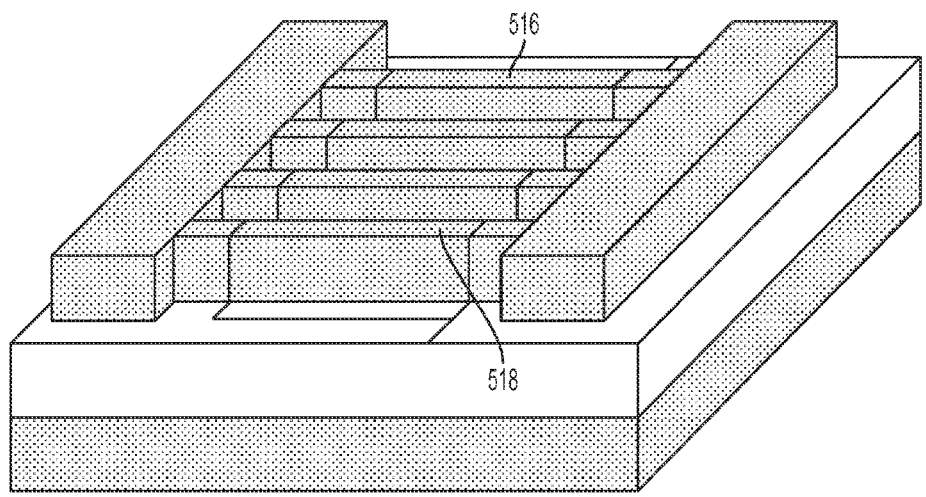

Sensitivity, accuracy, and repeatability of the finFET nanochannel biosensor may be significantly improved as shown in the embodiment coating procedures illustrated in FIGS. 5A through 5C.

In FIG. 5A a sensor area photoresist pattern 512 covers the sensor region 516 of the finFET transistor biosensor 502. The regions of the finFET biosensor 504, 506, and 510 that are exposed may be coated with anti-adhesion protective molecules such as polyelthylene glocol (PEG) terminated self assembled monolayers, benzene terminated self assembled monolayers, fluorocarbon molecules, or a thin layer of resist such as poly(methyl methacrylate) (PMMA) or S1813 (STO-609-acetic acid from Sigma-Aldrich), etc. The sensor area 516 covered by the sensor area photoresist pattern 512 occupies only a small fraction of the surface area that may be contacted by the sample solution or sample gas. If the target molecule is attracted to and adsorbed by surfaces outside the sensor area, a significant number of target molecules may be removed from the sample solution or gas changing the sample concentration before it reaches the sensor area. This may cause variation and errors in measurement of the target molecule concentration. By coating surfaces outside the sensor area with anti-adhesion protective molecules, the reproducibility, reliability, and sensitivity of the finFET biosensor may be significantly enhanced.

FIG. 5B shows the finFET biosensor 502 with the areas outside 514 the sensor area 516 coated with an anti-adhesion protective molecule and with the photoresist pattern 512 removed. The example embodiment shows a portion of the finFET nanochannels included in the sensor area, but the entire length of the finFET nanochannels may be included in the sensor area.

As shown in FIG. 5C, the sensor area 516 is then coated with sensor molecules 518 such as an antibody. In an example embodiment, linker molecules such as 11-(triethoxysilyl) undecanal (TESU) are first attached to the sensor area by soaking the finFET biosensor 502 in a solution containing the linker molecule. Solvents for the linker molecule may be toluene. Next a sensor molecule such as an antibody may be attached to the linker molecule binding sites by submersing the finFET biosensor 502 in a buffer solution containing the sensor molecule. If unused linker binding sites remain, the finFET biosensor 502 may then be immersed in a buffer solution containing linker blocker molecules which may attach to unused linker molecule binding sites thus blocking them. This prevents non target molecules in a sample from attaching to these sites. A non target molecule that attaches to a linker molecule may alter the charge on the gate of the finFET nanochannel causing variability and loss of selectivity. Blocking unused linker molecule binding sites improves the sensitivity, selectivity, and accuracy of the finFET biosensor 502.

Figure 6A:
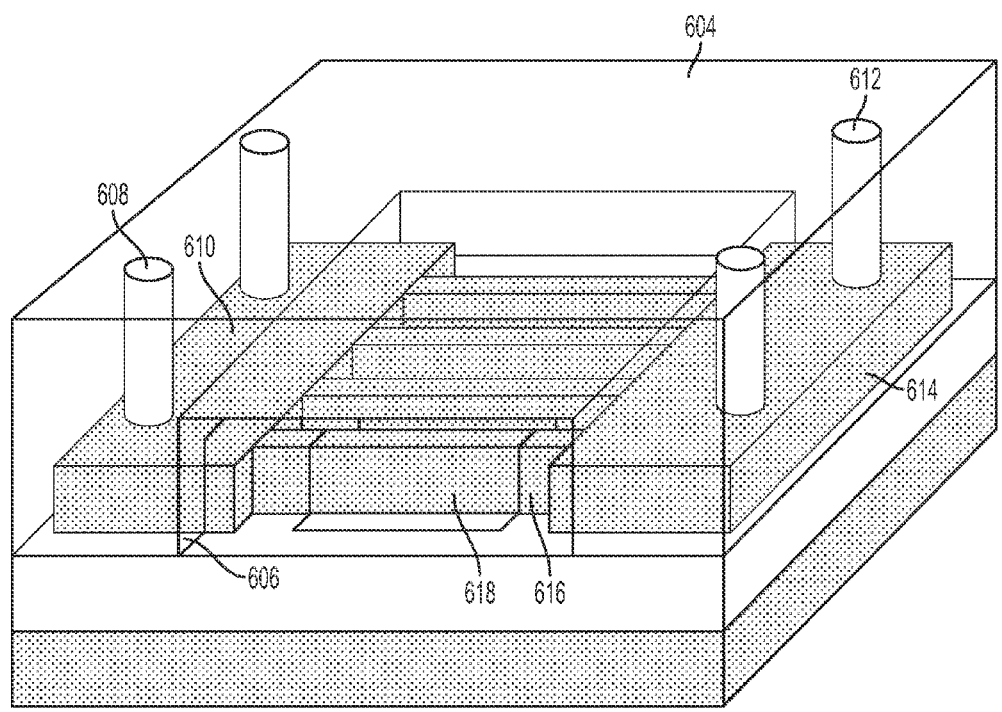
FIGS. 6A and 6B are illustrations of a finFET biosensor formed in accordance with an embodiment of the invention.
Figure 6B:
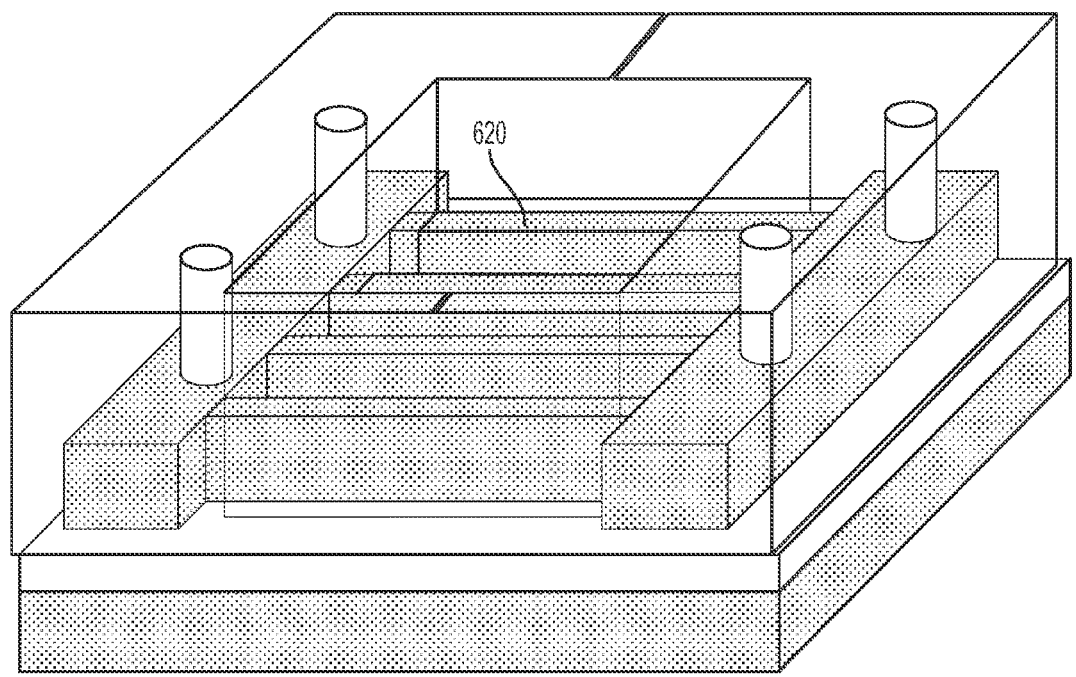

FIG. 6A shows an embodiment finFET biosensor 602 after additional processing. A dielectric layer 604 with a sample channel 606 is formed over the finFET biosensor 602. The dielectric may be silicon dioxide or silicon nitride or a plastic such as polyimide. Liquid or gaseous samples may flow through the sample channel 606 and over the sensor area 618 which is in the sample channel 606. Surface areas outside the sensor area 618, but within the sample channel 606 may be coated with anti-adhesion protective molecules. Contacts 608 to the source 610 and contacts 612 to the drain 614 of the finFET biosensor 602 are formed through the dielectric 604 and filled with a conductive material such as CVD-W, copper, or an aluminum alloy. Although the sample channel 606 is shown in this embodiment as a conduit 606 which flows over the sample area, other sample channel configurations such as an open-top well 620 in FIG. 6B may also be used.

Figure 7:
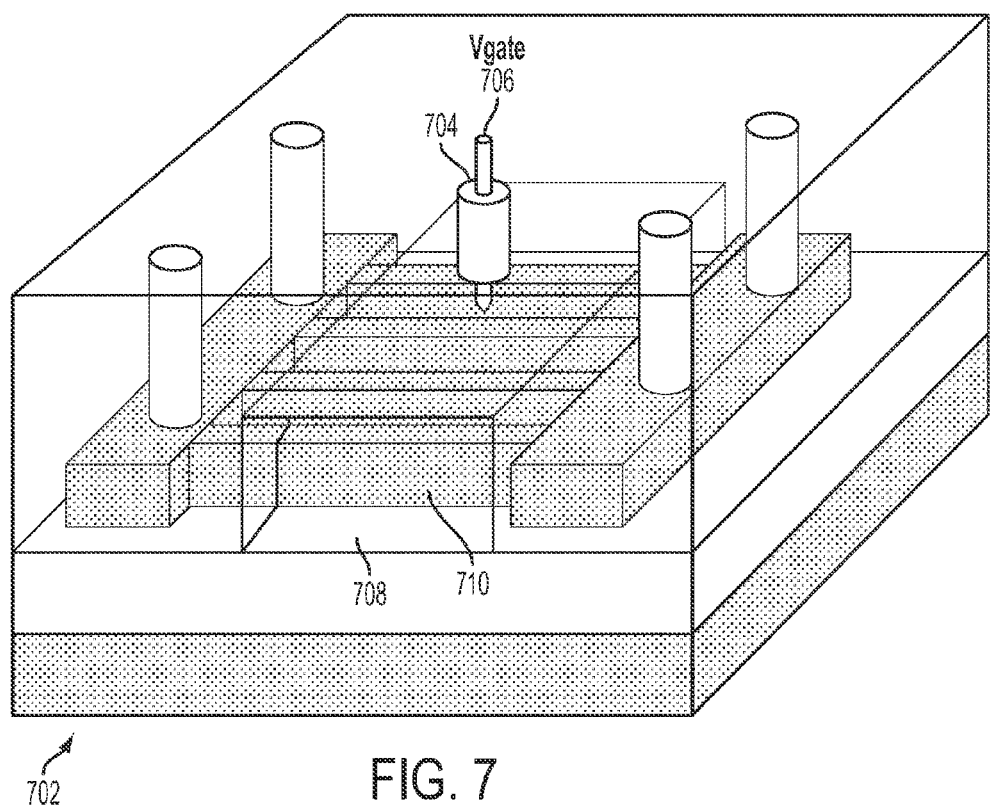
FIGS. 7, 8 and 9 are illustrations of a finFET biosensor with a gate biasing electrode formed in accordance with embodiments of the invention.

In the embodiment shown in FIG. 7, a biasing wire 704 extends into the sample channel 708. A voltage (Vgate) 706 may be applied to the biasing wire 704 to bias the finFET nanochannels 710 into the subthreshold region. A wire is an effective electrode for a liquid sample where the liquid is conductive, but may not be an effective electrode for gaseous samples. The biasing wire 704 is preferably formed of platinum or of a silver/silver chloride mixture.

Figure 8:
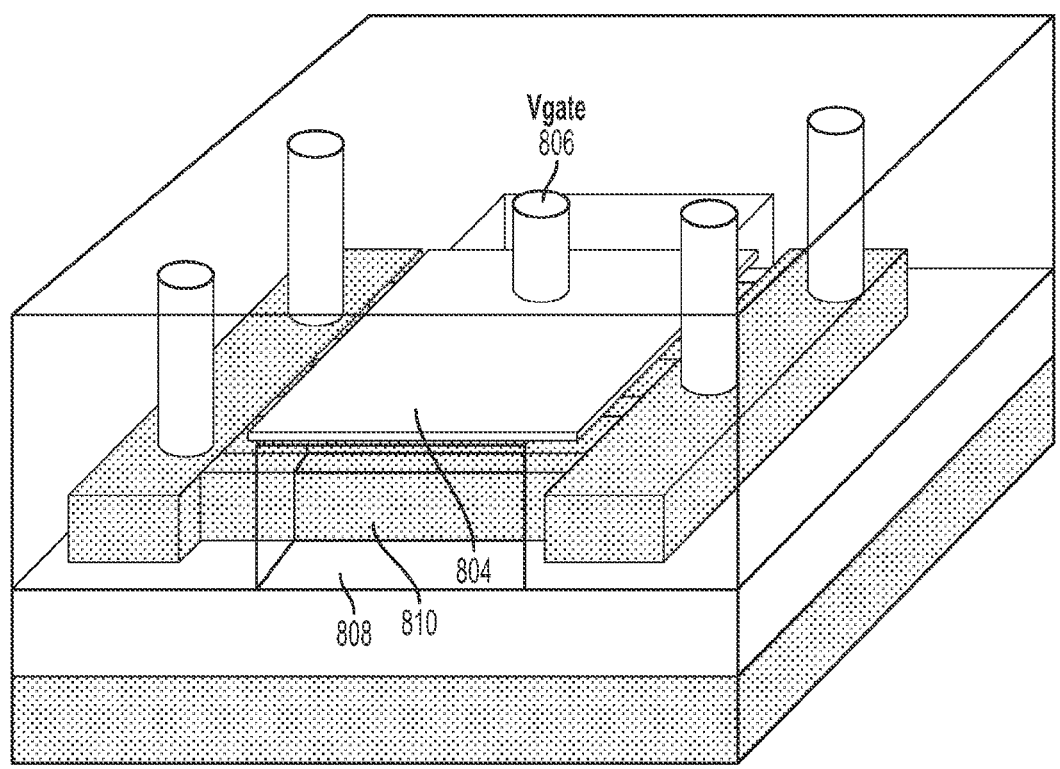

Another example embodiment with a biasing plate 804 over the finFET sensor area is shown in FIG. 8. A voltage (Vgate) 806 may be applied to the biasing plate 804 to bias the finFET nanochannels 810 into the subthreshold region. A biasing plate 804 may be an effective electrode for both liquid and gaseous samples. For liquid samples the biasing plate is preferably formed of platinum or of a silver/silver chloride mixture. For gaseous samples the biasing plate may be formed of any metallic material that does not react with the gaseous sample.

Figure 9:
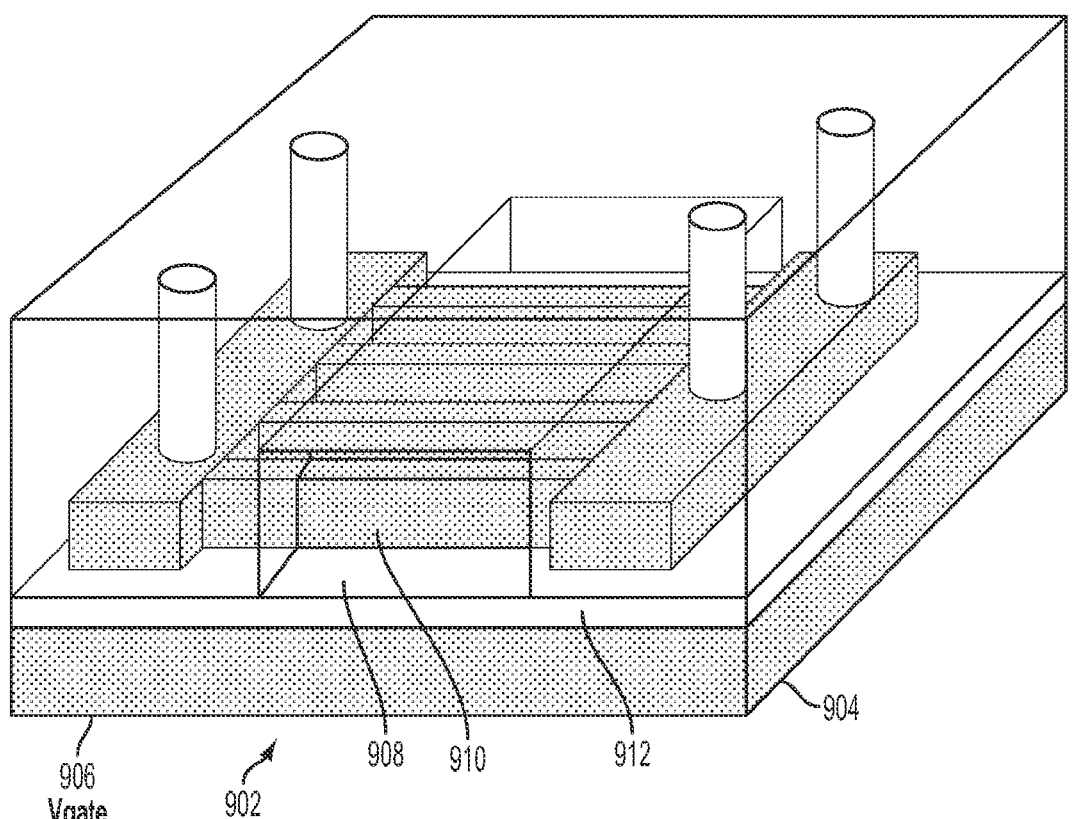

Another embodiment method of biasing the finFET nanochannels 910 into the subthreshold region is illustrated in FIG. 9. A biasing voltage 906 may be applied to the substrate 904 to bias the finFET nanochannels 910 into the subthreshold region using BOX 912 as the gate dielectric. For this biasing method, thinner BOX 912 is advantageous since it puts the biasing electrode 904 in closer proximity to the finFET nanochannels. This method of biasing may be used for both liquid and gaseous samples. This method may be the preferred method for gaseous samples.

Figure 16:
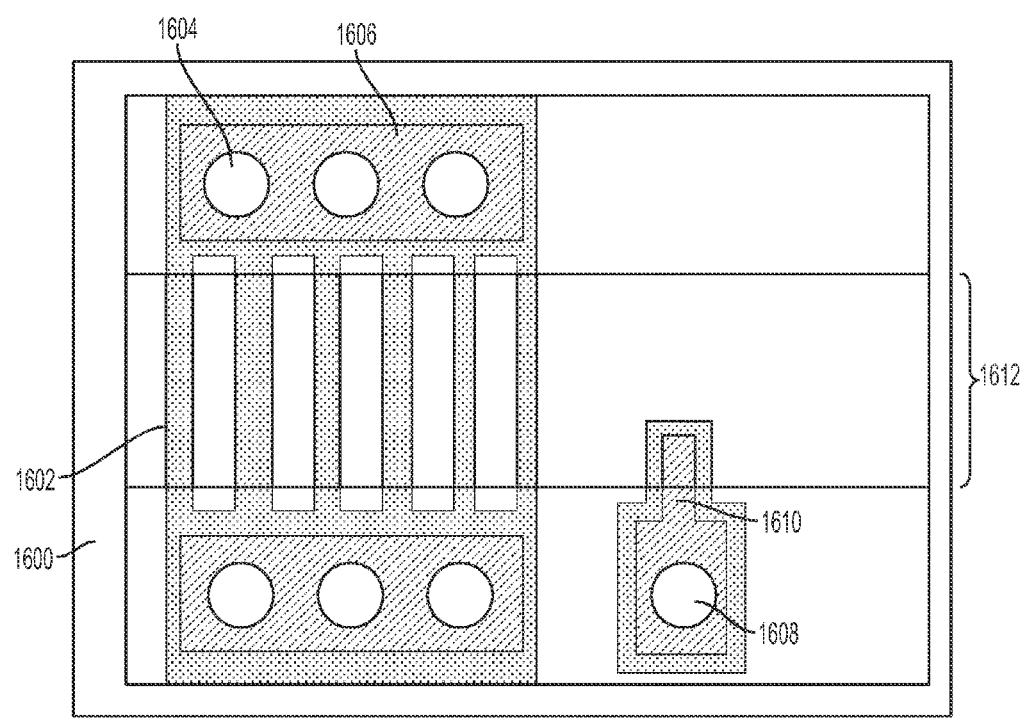
FIG. 16 is an illustration of a finFET biosensor with a gate biasing electrode formed in accordance with embodiments of the invention.

An additional embodiment method of biasing the finFET nanochannels 1602 into the subthreshold region is illustrated in FIG. 16. During processing, a micro-patterned electrode 1610 may be formed on the top surface of SOI substrate 1600 and beside the finFET biosensor extending into the sample channel 1612. The electrode 1610 may be formed of doped silicon; silicide such as titanium, nickel, or platinum; or metal. Contacts 1608 may be formed to the micro-patterned electrode 1610 at the same time as contacts 1604 are formed to the source and drain areas 1606 of the finFET biosensor.

Figure 17:
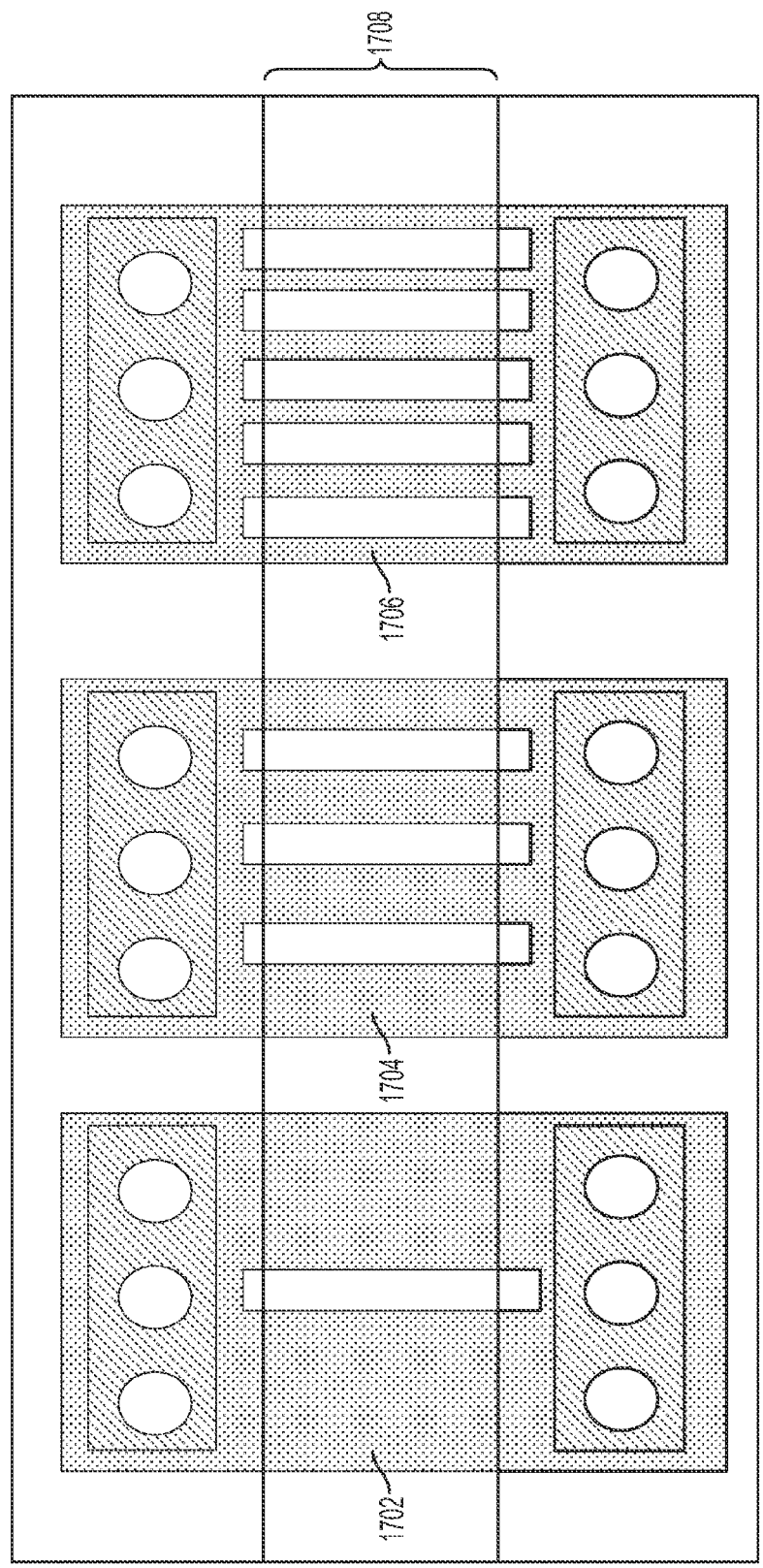
FIG. 17 is a finFET biosensor array formed in accordance with embodiments of the invention; and, FIG. 18 is a type of finFET biosensor array formed in accordance with embodiments of the invention.

A biosensor finFET array 1700 that enables the concentration of a target molecule to be measured over several orders of magnitude is shown in FIG. 17. The biosensor finFET array 1700 consists of a sample channel 1708 with several biosensor finFET transistors 1702, 1704, 1706 in the same sample channel 1708 with a range of fin widths. For example, the finFET transistor with wide fin width, 1702 may be optimized to measure target molecule concentrations in the micromolar to millimolar concentration range, the finFET transistor with intermediate fin width, 1704, may be optimized to measure target molecule concentrations in the nanomolar to micromolar concentration range, and the finFET transistor with narrow fin width, 1706, may be optimized to measure target molecule concentration in the picomolar to nanomolar concentration range. A finFET biosensor array 1700 with three finFET biosensor transistors each with a different fin width is used for illustration. finFET biosensor arrays with a different numbers of finFET biosensor transistors may be optimized to target various target molecule concentration ranges.

In the embodiment finFET biosensor array 1800 shown in FIG. 18, a first sensor molecule may be attached to the gate dielectric of the first finFET biosensor transistor 1802 and a second sensor molecule may be attached to the gate dielectric of the second finFET biosensor transistor 1804. In this way the concentration of two different target molecules may be measured in a sample which is in the sample channel 1806. More than two finFET biosensors each with a different sensor molecule attached to the gate dielectric may be used to measure the concentration of more than two target molecules in a sample.

While various embodiments of the present invention have been described above, it should be understood that they have been presented by way of example only and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

What is claimed is:
1. A finFET biosensor, comprising:
a semiconductor layer on a silicon-on-insulator (SOI) substrate;
a transistor source;
a transistor drain;

one or more finFET nanochannels formed in said semiconductor layer, wherein said nanochannels connect said transistor source and said transistor drain;
a gate dielectric covering a portion of said one or more nanochannels;
a sample channel; and
a sensor region further comprising a sensor molecule, wherein said sensor molecule is coupled to said gate dielectric, and further wherein the sensor region is located within the sample channel.

2. The finFET biosensor of claim 1 further comprising a layer of anti-adhesion protective molecules that coat the surface of said sample channel outside of said sensor region.

3. The finFET biosensor of claim 2 where said layer of anti-adhesion protective molecules is composed of polyethylene glocol (PEG) terminated self assembled monolayers, benzene terminated self assembled monolayers, fluorocarbon molecules, or a thin layer of resists comprising at least one of poly(methyl methacrylate) (PMMA) or S1813.

4. The finFET biosensor of claim 1 where said sensor molecule is an antibody, an antigen, a protein, a receptor, an aptamer, a peptide, a DNA strand, or an enzyme.

5. The finFET biosensor of claim 1 where said sensor molecule is an antibody.

6. The finFET biosensor of claim 1 where said sensor molecule is an antigen.

7. The finFET biosensor of claim 1 further comprising a biasing electrode.

8. The finFET biosensor of claim 1 where said finFET is a nmos or pmos enhancement mode transistor.

9. The finFET biosensor of claim 1 where said finFET is a nmos or pmos depletion mode transistor.

10. The finFET biosensor of claim 1 where said gate dielectric is composed of silicon dioxide, silicon nitride, $Al_2O_3$, $HfO_2$, or silicon oxynitride, and the gate dielectric has a thickness of 0.5-20 nm.

11. The finFET biosensor of claim 1 where said sensor molecule is coupled to said gate dielectric using a linker molecule.

12. A finFET biosensor, comprising:
a substrate comprising a semiconductor layer on a silicon-on-insulator (SOI) material;
a transistor source directly on the substrate and extending away from a surface of the substrate;
a transistor drain directly on the substrate and extending away from the surface of the substrate;
one or more finFET nanochannels formed in said semiconductor layer, wherein said one or more nanochannels connect said transistor source and said transistor drain, wherein the one or more nanochannels are directly on the substrate and extend away from the surface of the substrate;
a gate dielectric disposed directly on the one or more nanochannels;
a sample channel, wherein the one or more finFET nanochannels are within the sample channel; and
a sensor region further comprising a sensor molecule, wherein said sensor molecule is coupled to said gate dielectric, and further wherein the sensor region is located within the sample channel.

13. The finFET biosensor of claim 12 further comprising a layer of anti-adhesion protective molecules that coat the surface of said sample channel outside of said sensor region.

14. The finFET biosensor of claim 13 where said layer of anti-adhesion protective molecules is composed of polyethylene glocol (PEG) terminated self assembled monolayers, benzene terminated self assembled monolayers, fluorocarbon molecules, or a thin layer of resists comprising at least one of poly(methyl methacrylate) (PMMA) or S1813.

15. The finFET biosensor of claim 12 where said sensor molecule is an antibody, an antigen, a protein, a receptor, an aptamer, a peptide, a DNA strand, or an enzyme.

16. The finFET biosensor of claim 12 where said sensor molecule is an antibody.

17. The finFET biosensor of claim 12 where said sensor molecule is an antigen.

18. The finFET biosensor of claim 12 further comprising a biasing electrode.

19. The finFET biosensor of claim 12 where said finFET is a nmos or pmos enhancement mode transistor.

20. The finFET biosensor of claim 12 where said finFET is a nmos or pmos depletion mode transistor.

21. The finFET biosensor of claim 12 where said sensor molecule is coupled to said gate dielectric using a linker molecule.

* * * * *